(12) United States Patent
Zou et al.

(10) Patent No.: US 10,864,210 B2
(45) Date of Patent: Dec. 15, 2020

(54) COMPOSITION AND COMBINED MEDICATION METHOD FOR TREATING ENTEROVIRUS INFECTION

(71) Applicant: Institut Pasteur of Shanghai, Chinese Academy of Sciences, Shanghai (CN)

(72) Inventors: Gang Zou, Shanghai (CN); Ralf Altmeyer, Shanghai (CN); Yizhuo Wang, Shanghai (CN)

(73) Assignee: INSTITUT PASTEUR OF SHANGHAI, CHINESE ACADEMY OF SCIENCES, Shanghai (CN)

( * ) Notice: Subject to any disclaimer, the term of this patent is extended or adjusted under 35 U.S.C. 154(b) by 0 days.

(21) Appl. No.: 16/073,487

(22) PCT Filed: Jan. 11, 2017

(86) PCT No.: PCT/CN2017/070858
§ 371 (c)(1),
(2) Date: Jul. 27, 2018

(87) PCT Pub. No.: WO2017/128950
PCT Pub. Date: Aug. 3, 2017

(65) Prior Publication Data
US 2019/0030027 A1    Jan. 31, 2019

(30) Foreign Application Priority Data

Jan. 29, 2016  (CN) .......................... 2016 1 0067164
Jan. 29, 2016  (CN) .......................... 2016 1 0067175

(51) Int. Cl.
A61K 31/4965     (2006.01)
A61K 31/185      (2006.01)
(Continued)

(52) U.S. Cl.
CPC ........ *A61K 31/4965* (2013.01); *A61K 31/185* (2013.01); *A61K 31/422* (2013.01); *A61K 31/496* (2013.01); *A61K 45/06* (2013.01); *A61P 31/14* (2018.01); *C12N 7/00* (2013.01); *G01N 33/56983* (2013.01);
(Continued)

(58) Field of Classification Search
None
See application file for complete search history.

(56) References Cited

FOREIGN PATENT DOCUMENTS

| | | |
|---|---|---|
| CN | 103145608 A | 6/2013 |
| CN | 105664166 A | 6/2016 |
| CN | 105688216 A | 6/2016 |

OTHER PUBLICATIONS

Sun et al. (Antimicrobial Agents and Chemotherapy, Dec. 2015, p. 7782-7784).*

(Continued)

*Primary Examiner* — Agnieszka Boesen
(74) *Attorney, Agent, or Firm* — Panitch Schwarze Belisario & Nadel LLP (57) ABSTRACT

The present invention provides a composition and a combined medication method for treating an enterovirus infection. In particular, the present invention provides a composition for inhibiting enteroviruses, wherein the composition at least contains an inhibitor of a 3D virus protein and an inhibitor of a capsid protein, or a combination of an inhibitor of a 3C protein and an inhibitor of a 3A protein.

8 Claims, 5 Drawing Sheets

Specification includes a Sequence Listing.

(51) Int. Cl.
*C12N 7/00* (2006.01)
*A61K 45/06* (2006.01)
*A61P 31/14* (2006.01)
*A61K 31/422* (2006.01)
*A61K 31/496* (2006.01)
*G01N 33/569* (2006.01)

(52) U.S. Cl.
CPC .............. *C12N 2770/00021* (2013.01); *G01N 2333/085* (2013.01); *G01N 2500/04* (2013.01)

(56) References Cited

OTHER PUBLICATIONS

Rhoden et al. (Antiviral Research 2013, p. 186-191).*
Albulascu et al. (Antiviral Research, 2015, p. 39-46).*
Furuta et al, "Favipiravir (T-705), a novel viral RNA polymerase inhibitor," Antiviral Res., vol. 100, pp. 446-454 (2013).
Prichard et al, "Three-Dimensional Analysis of the Synergistic Cytotoxicity of Ganciclovir and Zidovudine," Antimicrobial Agents and Chemotherapy, vol. 35, No. 6, pp. 1060-1065 (Jun. 1991).
Int'l Search Report dated Apr. 20, 2017 in Int'l Application No. PCT/CN2017/070858.
Wang et al, "In Vitro Assessment of Combinations of Enterovirus Inhibitors against Enterovirus 71," Antimicrobial Agents and Chemotherapy, vol. 60, No. 9, pp. 5357-5367 (Sep. 2016).
Sadeghipour et al, "Ribavirin-Resistant Mutants of Human Enterovirus 71 Express a High Replication Fidelity Phenotype during Growth in Cell Culture," Journal of Virology, vol. 87, No. 3, pp. 1759-1769 (Feb. 2013).
Qiao et al, "Advances Research in 3D Protein of Enterovirus 71," Chinese Journal of Zoonoses, vol. 31, No. 8, pp. 763-765 (Aug. 2015).
Gao et al., "Discovery of Itraconazole with Broad-Spectrum In Vitro Antienterovirus Activity that Targets Nonstructural Protein 3A," Antimicrobial Agents and Chemotherapy, vol. 59, No. 5, p. 2654 (May 2015) (Abstract Only).
Office Action dated Jan. 17, 2018 in CN Application No. 201610067175.3.
Office Action dated Feb. 12, 2018 in CN Application No. 201610067164.5.
Office Action dated Jul. 31, 2018 in CN Application No. 201610067164.5.
Office Action dated Sep. 29, 2018 in CN Application No. 201610067175.3.
Rocha-Pereira et al., "The Enterovirus Protease Inhibitor Rupintrivir Exerts Cross-Genotypic Anti-Norovirus Activity and Clears Cells from the Norovirus Replicon," Antimicrobial Agents and Chemotherapy, vol. 58, No. 8, pp. 4675-4681 (Aug. 2014) (Abstract Only).
Zhang et al., "Rupintrivir is a promising candidate for treating severe cases of enterovirus-71 infection: Evaluation of antiviral efficacy in a murine infection model," Antiviral Research, vol. 97, pp. 264-269 (2013) (Abstract Only).
Zhang et al., "Advances in research on anti-enteric virus 71 treatment strategy," Chin. I Exp. Infect. Dis (Electronic Edition), vol. 8, No. 5, pp. 715-718 (Oct. 2014).
Zhao et al., "A new antiviral drng-Favipiravir," Clinical Medication Journal, vol. 13, No. 4, pp. 16-20 (Jul. 2015) (First Page English Abstract).
Shang et al., "An adenosine nucleoside analogue NITD008 inhibits EV71 proliferation," Antiviral Research, vol. 112, pp. 47-58 (2014).
English Translation of Written Opinion dated Dec. 19, 2019 in SG Application No. 11201806433V.
Ren et al., "The approved pediatric drug suramin identified as a clinical candidate for the treatment of EV71 infection-suramin inhibits EV71 infection in vitro and in vivo." Emerging Microbes and Infections, vol. 3, pp. 1-9 (2014).

\* cited by examiner

A itraconazole -GW5074

B itraconazole - suramin

C suramin- rupintrivir

D favipiravir- rupintrivir

E favipiravir - suramin

F itraconazole - favipiravir

G itraconazole - rupintrivir

COMPOSITION AND COMBINED MEDICATION METHOD FOR TREATING ENTEROVIRUS INFECTION

CROSS-REFERENCE TO RELATED APPLICATION

This application is a Section 371 of International Application No. PCT/CN2017/070858, filed Jan. 11, 2017, which was published in the Chinese language on Aug. 3, 2017, under International Publication No. WO 2017/128950 A1, which claims priority under 35 U.S.C. § 119(b) to Chinese Application No. 2016-10067164.5, filed Jan. 29, 2016 and Chinese Application No. 2016-10067175.3, filed Jan. 29, 2016, the disclosures of which are incorporated herein by reference in their entirety.

REFERENCE TO SEQUENCE LISTING SUBMITTED ELECTRONICALLY

This application contains a sequence listing, which is submitted electronically via EFS-Web as an ASCII formatted sequence listing with a file name "Sequence Listing", creation date of Jul. 25, 2018, and having a size of about 4.4 KB The sequence listing submitted via EFS-Web is part of the specification and is herein incorporated by reference in its entirety.

TECHNICAL FIELD

The present invention belongs to the field of biomedicine, and in particular, the present invention relates to a composition and a combined medication method for treating enterovirus infection.

BACKGROUND ART

Enterovirus is a virus of the picornavirus family with a single positive strand RNA, and more than 100 serotypes have been found. Most enterovirus infections do not cause serious symptoms or only cause milder diseases, but often have serious consequences in children and immunodeficiency populations. Enterovirus 71 (EV74) and Coxsackievirus A16 (CVN16) in the genus Enterovirus are main pathogens causing hand-foot-mouth disease in infants and young children in Asia-Pacific region. Symptoms of hand-foot-mouth disease are usually mild, such as fever, pharyngalgia, diarrhea, local rash and the like, but some patients develop central nervous system (CNS) diseases such as aseptic meningitis, lethal encephalitis and even death. EV71 is the main pathogen causing severe hand-foot-mouth disease. So far, there is no effective drug treatment for enterovirus infection. The existing treatment is limited to supportive care, intravenous injection of immunoglobulin or ribavirin. Therefore, it is extremely urgent to find antiviral medicaments. Enteroviruses use the virus's own RNA-dependent RNA polymerase to synthesize the genome, so progeny RNA is susceptible to mutation during RNA replication.

Therefore, in order to effectively prevent or treat enterovirus infection, there is an urgent need in the art to develop novel techniques for preventing and/or treating enterovirus infection.

SUMMARY OF THE PRESENT INVENTION

The object of the present invention is to provide a component and a combined medication method for treating enterovirus infection.

The first aspect of the present invention provides a composition for inhibiting enterovirus, including a first active ingredient and a second active ingredient, wherein the first active ingredient is an inhibitor of 3D protein of enterovirus (eg, EV71);

the second active ingredient is an inhibitor of capsid protein of enterovirus (eg, EV71);

or wherein the first active ingredient is an inhibitor of 3C protein of enterovirus (eg, EV71);

the second active ingredient is selected from the group consisting of:

an inhibitor of 3A protein of enterovirus (eg, EV71); and an inhibitor of 3D protein of enterovirus (eg, EV71).

In another preferred embodiment, the composition includes a first active ingredient and a second active ingredient, wherein the first active ingredient is an inhibitor of 3D protein of enterovirus (eg, EV71);

the second active ingredient is an inhibitor of capsid protein of enterovirus (eg, EV71).

In another preferred embodiment, the first active ingredient specifically binds to the amino acid residue (preferably a serine residue) at position 121 of 3D protein of enterovirus, wherein the amino acid residue is numbered based on SEQ ID NO: 1.

In another preferred embodiment, the first active ingredient includes favipiravir, an analog thereof, or a pharmaceutically acceptable salt thereof;

the second active ingredient comprises suramin, an analog thereof, or a pharmaceutically acceptable salt thereof.

In another preferred embodiment, the analog of favipiravir includes a substance which acts on the same target of enterovirus as favipiravir.

In another preferred embodiment, the analog of suramin includes a substance which acts on the same target of enterovirus as suramin.

In another preferred embodiment, the enterovirus is selected from the group consisting of enterovirus 71 (EV71), coxsackievirus A16 (CVA16), CVB3, PV1 or EV68, and rhinovirus.

In another preferred embodiment, the molar ratio of the first active ingredient to the second active ingredient is about 10-100: 1-20, preferably 10-100: 1-10, and more preferably 10-100: 1-5.

In another preferred embodiment, the first active ingredient has an inhibitory activity towards 3D protein of enterovirus (e.g., EV71).

In another preferred embodiment, the second active ingredient has an inhibitory activity towards capsid protein of enterovirus (e.g., EV71).

In another preferred embodiment, the composition further includes a pharmaceutically acceptable carrier or excipient.

In another preferred embodiment, the dosage form of the pharmaceutical composition comprises tablet, granule, capsule, pill, injection, or oral solution.

In another preferred embodiment, the composition is a unit dosage form, and the content of the first active ingredient and the second active ingredient in each unit dosage form is about 0.1-1 (or 0.25-1, or 0.5-1) of a daily dose, wherein the daily dose is 20-100 mg.

In another preferred embodiment, the daily dose is 25-70 mg, such as 25 mg, 40 mg, 50 mg.

In another preferred embodiment, the composition includes a first active ingredient and a second active ingredient, where, the first active ingredient is an inhibitor of 3C protein of enterovirus (eg, EV71);

the second active ingredient is selected from the group consisting of:

an inhibitor of 3A protein of enterovirus (eg, EV71); and
an inhibitor of 3D protein of enterovirus (eg, EV71).

In another preferred embodiment, the first active ingredient includes rupintrivir, an analog thereof, or a pharmaceutically acceptable salt thereof;

the second active ingredient is selected from the group consisting of itraconazole, an analog thereof, or a pharmaceutically acceptable salt thereof; and favipiravir, an analog thereof, or a pharmaceutically acceptable salt thereof.

In another preferred embodiment, the analog of rupintrivir includes a substance which acts on the same target of enterovirus as rupintrivir (eg, AG7404).

In another preferred embodiment, the analog of itraconazole includes a substance which acts on the same target of enterovirus as itraconazole.

In another preferred embodiment, the enterovirus is selected from the group consisting of enterovirus 71 (EV71), coxsackievirus A16 (CVA16), CVB3, PV1 or EV68, and rhinovirus.

In another preferred embodiment, the molar ratio of the first active ingredient to the second active ingredient is about 1-20:10-100, preferably 1-10:10-100, and more preferably 1-5:10-100.

In another preferred embodiment, the first active ingredient has an inhibitory activity towards 3C protein of enterovirus (e.g., EV71).

In another preferred embodiment, the second active ingredient has an inhibitory activity towards 3A protein and/or 3D of enterovirus (e.g., EV71). In the present invention, itraconazole has a 3A protein inhibitory activity, and favipiravir has a 3D protein inhibitory activity.

In another preferred embodiment, the composition further includes a pharmaceutically acceptable carrier or excipient.

In another preferred embodiment, the dosage form of the pharmaceutical composition comprises tablet, granule, capsule, pill, injection, or oral solution.

In another preferred embodiment, the composition is a unit dosage form, and the content of the first active ingredient and the second active ingredient in each unit dosage form is about 0.1-1 (or 0.25-1, or 0.5-1) of a daily dose, wherein the daily dose is 20-100 mg.

In another preferred embodiment, the daily dose is 25-70 mg, such as 25 mg, 40 mg, 50 mg.

The second aspect of the present invention provides use of the composition for inhibiting enterovirus according to the first aspect of the present invention for the manufacture of a medicament for preventing and/or treating an enterovirus infection.

The third aspect of the present invention provides a method of preventing and/or treating an enterovirus infection, comprising the step of:

administering the composition for inhibiting enterovirus according to the first aspect of the present invention to a subject in need thereof, thereby inhibiting enterovirus in the body of the subject.

In another preferred embodiment, the subject comprises a human and a non-human mammal (e.g., a rodent).

In another preferred embodiment, the administration is carried out in an amount of 10 to 100 mg/kg body weight, preferably 15 to 70 mg/kg body weight, more preferably 10 to 50 mg/kg body weight, based on the weight of the first active ingredient.

The fourth aspect of the present invention provides a method for non-therapeutically inhibiting enterovirus growth or killing enterovirus in vitro comprising the step of: applying the composition for inhibiting enterovirus according to the first aspect of the present invention in a place that needs to be treated.

The fifth aspect of the present invention provides use of favipiravir, an analogue thereof, or a pharmaceutically acceptable salt thereof for the manufacture of a reagent used for:

(I) inhibiting the synthesis of enterovirus 3D protein, and/or (II) specifically binding to amino acid residue at position 121 of enterovirus 3D protein, wherein the amino acid residue is numbered based on SEQ ID NO: 1.

In another preferred embodiment, the amino acid residue at position 21 of enterovirus 3D protein is serine.

In another preferred embodiment, the agent is further used for: (III) inhibiting the replication of enterovirus.

In another preferred embodiment, the enterovirus is enterovirus 71.

The sixth aspect of the present invention provides a complex as shown in formula I, $$A\text{-}B \qquad (I)$$

wherein A is favipiravir or an analog thereof; and B is a 3D protein of enterovirus.

In another preferred embodiment, in the complex, the binding site of A and B includes the amino acid residue at position 121 of enterovirus 3D protein, wherein the amino acid residue is numbered based on SEQ ID NO: 1.

The seventh aspect of the present invention provides a drug-resistant enterovirus strain, wherein 3D protein of the strain is mutated, and the mutation causes the enterovirus to develop drug resistance.

In another preferred embodiment, the mutation occurs at the amino acid residue at position 121 of the 3D protein.

In another preferred embodiment, the amino acid residue at position 121 of the 3D protein is mutated from a serine residue to an aspartic acid residue.

In another preferred embodiment, the strain is an enterovirus 71 strain.

The eighth aspect of the present invention provides use of drug-resistant enterovirus strain of the seventh aspect of the present invention for screening an agent or a reagent for inhibiting or killing enterovirus.

The ninth aspect of the present invention provides an inhibitor of the drug-resistant enterovirus strain of the present invention, and the inhibitor can inhibit or kill the drug-resistant enterovirus strain of the seventh aspect of the present invention.

The tenth aspect of the present invention provides a method for screening a madicament comprising: contacting a madicament to be screened with enterovirus or 3D protein of enterovirus, and detecting whether a complex of the formula II is formed, $$A'\text{-}B \qquad (II)$$

wherein A' is the madicament to be screened; and B is the 3D protein of enterovirus.

In another preferred embodiment, in the complex, the binding site of A' and B includes amino acid residue at position 121 of enterovirus 3D protein, wherein the amino acid residue at position 121 is based on SEQ ID NO: 1.

In another preferred embodiment, the madicament to be screened includes, for example, favipiravir, an analog thereof, or a pharmaceutically acceptable salt thereof.

The eleventh aspect of the present invention provides an enterovirus inhibitor which targets 3D protein of enterovirus and inhibits the growth or reproduction of the enterovirus.

In another preferred embodiment, the inhibitor targets amino acid residue at position 121 of enterovirus 3D protein, wherein the amino acid residue at position 121 is based on SEQ ID NO: 1.

In another preferred embodiment, the inhibitor is selected from the group consisting of favipiravir, an analog thereof, or a pharmaceutically acceptable salt thereof.

It should be understood that within the scope of the present invention, the above each technical feature of the present invention and each technical feature specifically described in the following (such as the examples) can be combined with each other to constitute a new or preferred technical solution. Due to space limitations, it will not be described one by one here.

DESCRIPTION OF THE DRAWINGS

FIG. 1 shows that itraconazole, rupintrivir, favipiravir, suramin, and GW5074 inhibit EV71 infection, wherein

DETAILED DESCRIPTION OF THE INVENTION

Through extensive and intensive research, the inventors firstly and unexpectedly discovered a composition for inhibiting enterovirus, the composition comprises favipiravir as the first active ingredient and suramin as the second active ingredient, or the composition comprises rupintrivir as the first active ingredient and itraconazole and/or favipiravir as the second active ingredient. The experiment results show that the medicament combination has a significant synergistic effect, and no enhanced cytotoxicity is observed under the tested concentration combination.

The present invention discloses a combined medication method for effectively inhibiting enterovirus infection. For the inhibitory activity of enteroviruses, the inventors have unexpectedly discovered that favipiravir and suramin, rupintrivir and itraconazole, rupintrivir and favipiravir show significant synergy through extensive tests. Moreover, no enhanced cytotoxicity is observed under the tested concentration combination for above medicament combination. The combination of favipiravir and suramin or the combination of rupintrivir and itraconazole can prevent the emergence of resistant viruses. In addition, the inventors have also found that favipiravir inhibits viral replication by acting on the 3D protein of EV71, which can be used as a potential target for the development of antiviral medicaments.

Before describing the present invention, it is to be understood that this invention is not limited to the particular methods and experimental conditions described as such methods and conditions may vary. It is also understood that the terms used herein is for the purpose of describing the particular embodiments, and is not intended to be used for limit, and the scope of the invention is limited only by the appended claims.

Unless otherwise defined, all technical and scientific terms used herein have the same meaning as commonly understood by one of ordinary skill in the art to which this invention belongs. As used herein, the term "about", when being used in reference to a particular recited value, means that the value can vary by no more than 1% from the recited value. For example, as used herein, the expression "about 1.00" includes all values between 99 and 101 (for example, 99.1, 99.2, 99.3, 99.4, etc.).

Although any methods and materials similar or equivalent to those described in the present invention can be used in the examples or tests of the present invention, the preferred methods and materials are provided herein.

Favipiravir and Analog Thereof

Favipiravir is a RdRP inhibitor with broad spectrum antiviral activity. After intensive research, the inventors unexpectedly found that favipiravir can inhibit EV71 replication in vitro, and the mechanism studies have found that its site of action is located in the 3D protein of EV71.

In a preferred embodiment of the present invention, the analog of favipiravir according to the present invention comprises a substance which acts on the same target of enterovirus as favipiravir.

In a preferred embodiment of the present invention, the present invention provides an inhibitor of enterovirus, which targets the enterovirus 3D protein and inhibits the growth or reproduction of the enterovirus.

In a preferred embodiment, the inhibitor targets amino acid residue at position 121 of 3D protein of enterovirus, wherein the amino acid residue is numbered based on SEQ ID NO: 1

In a preferred embodiment, the inhibitor is selected from the group consisting of favipiravir, an analog thereof, or a pharmaceutically acceptable salt thereof.

3D protein is an enterovirus (EV71 virus) RNA-dependent RNA polymerase and is an important enzyme encoded by the viral genome, which catalyzes the replication and transcription of the viral genome. In a preferred embodiment of the present invention, the amino acid sequence of the 3D protein is as follows:

(SEQ ID NO: 1)
GEIQWVKPNKETGRLNINGPTRTKLEPSVFHDIFEGNKEPAVLHSKDPRL

EVDFEQALFSKYVGNTLYEPDEYIKEAALHYANQLKQLEINTSQMSMEEA

CYGTENLEAIDLHTSAGYPYSALGIKKRDILDPTTRDVSKMKFYMDKYGL

DLPYSTYVKDELRSIDKIKKGKSRLIEASSLNDSVYLRMTFGHLYEAFHA

NPGTITGSAVGCNPDTFWSKLPILLPGSLFAFDYSGYDASLSPVWFRALE

LVLREIGYSERAVSLIEGINHTHHVYRNKTYCVLGGMPSGCSGTSIFNSM

```
INNIIIRALLIKTFKGIDLDELNMVAYGDDVLASYPFPIDCLELAKTGKE

YGLTMTPADKSPCFNEVNWGNATFLIKRGFLPDEQFPFLIHPTMPMRIHE

SIRWTKDARNTQDHVRSLCLLAWHNGKQEYEKFVSTIRSVPVGRALAIPN

YENLRRNWLELF
```

Suramin and Analog Thereof

Suramin is clinically used to treat trypanosomiasis and acts with the capsid protein of EV71 to inhibit viral adsorption into cells.

In a preferred embodiment of the present invention, the analog of suramin according to the present invention has the structure shown in the following formula IV:

In a preferred embodiment of the present invention, the analog of suramin according to the present invention comprises a substance which acts on the same target of enterovirus as suramin (for example, NF449, Nf110 and NM16).

NF449

NF110

NM16

Rupintrivir and Analog Thereof

Rupintrivir was originally used to treat rhinovirus infection, and studies have shown that it inhibits viral replication primarily by inhibiting the 3C protein of EV71.

In a preferred embodiment of the present invention, the analog of rupintrivir according to the present invention, AG7404, has the following structure:

In a preferred embodiment of the present invention, the analog of rupintrivir according to the present invention comprises a substance which acts on the same target of enterovirus as rupintrivir (eg AG7404).

Itraconazole and Analog Thereof

Itraconazole is an oral triazole broad-spectrum antifungal agent that inhibits *Aspergillus* and *Candida albicans* and is effective in treating fungal infections in children. It is also a recently reported broad-spectrum enterovirus inhibitor that inhibits the viral life cycle by acting on the 3A protein of the virus and the oxidative sterol-binding protein of the host.

In a preferred embodiment of the present invention, the analog of itraconazole according to the present invention comprises a substance which acts on the same target of enterovirus as itraconazole.

GW5074 and Analog Thereof

GW5074 is a Raf signaling pathway kinase inhibitor that has an inhibitory effect on enterovirus replication but does not act on this cellular pathway. It exerts antiviral activity by acting on the 3A protein of poliovirus.

The structural formulas of the compounds involved in the present application are as follows: 1 is itraconazole, 2 is rupintrivir, 3 is favipiravir, 4 is GW5074, and 5 is suramin.

1

2

3

4

5

In the combined medication method, suramin and favipiravir as well as itraconazole and rupintrivir show significant synergistic effect, and no significant enhanced cytotoxicity is detected at the measured concentration; rupintrivir and favipiravir show a weak synergistic effect; rupintrivir and suramin show an additive effect; and itraconazole and suramin, itraconazole and favipiravir, GW5074 and itraconazole show strong antagonistic effect.

Composition

The term "composition," as used herein, includes a pharmaceutical composition.

The composition of the first aspect of the present invention comprises an active ingredient which inhibits enterovirus, and a pharmaceutically acceptable carrier. The active ingredient for inhibiting enterovirus comprises a first active ingredient and a second active ingredient, wherein the first active ingredient comprises favipiravir, an analog thereof, or a pharmaceutically acceptable salt thereof; and the second active ingredient is selected from the group consisting of suramin, an analog thereof, or a pharmaceutically acceptable salt thereof; and rupintrivir, an analog thereof, or a pharmaceutically acceptable salt thereof.

The pharmaceutical composition of the present invention may further comprise various pharmaceutical excipients compatible with the compound or composition contained therein, and is prepared into a dosage form which is advantageous for administration by a conventional method, such as, but not limited to, aqueous solution injection, powder injection, pill, powder, tablet, patch, suppository, emulsion, cream, gel, granule, capsule, aerosol, spray, powder spray, sustained release preparation, controlled release preparation and the like. The pharmaceutical excipients may be conventionally used in various preparations, such as, but not limited to, isotonic agent, buffer, flavoring agent, excipients, filler, binder, disintegrator, lubricant, and the like; or may be selected for use in accordance with the substance, such as: but not limited to emulsifier, solubilizer, bacteriostatic agent, analgesic, antioxidants and the like. Such excipients can effectively improve the stability and solubility of the compound contained in the composition, or change the release rate and absorption rate of the compound to improve the metabolism of various compounds in the organism, thereby enhancing the administration effect of the composition. In addition, excipients such as, but not limited to, gelatin, albumin, chitosan, polyethers and polyesters (such as, but not limited to, polyethylene glycol, polyurethane, polycarbonate and copolymers thereof) may be used for achieving specific administration purposes or modes such as sustained release administration, controlled release administration, pulse administration and the like.

The main manifestations to facilitate administration are: but not limited to, improving the therapeutic effect, improving bioavailability, reducing toxic side effect, improving patient compliance and the like.

In the case of aqueous injection, the excipient generally includes isotonic agent and buffer, as well as the necessary emulsifier (eg, Tween-80, Pluronic, and Poloxamer, etc.) solubilizer, bacteriostatic agent and the like. In addition, it also includes other pharmaceutically acceptable excipient such as antioxidant, adjuster, analgesic and the like.

The excipient used in the preparation of oral liquid preparation generally includes solvent, as well as the necessary flavoring, bacteriostatic, emulsifying, and coloring agent.

The excipient used in the preparation of tablet generally includes filler (eg, starch, powdered sugar, dextrin, lactose, compressible starch, microcrystalline cellulose, calcium sulfate, calcium hydrogen phosphate, mannitol, etc.), binder (eg ethanol, starch slurry, sodium carboxymethyl cellulose, hydroxypropyl cellulose, methylcellulose, ethyl cellulose, hydroxypropylmethyl cellulose, gelatin solution, sucrose solution and aqueous solution or alcohol solution of polyvinylpyrrolidone, etc.), disintegrant (such as dry starch, sodium carboxymethyl starch, low-substituted hydroxypropyl cellulose, cross-linked polyvinylpyrrolidone and croscarmellose sodium) and lubricant (such as magnesium stearate, micronized silica gel, talc, hydrogenated vegetable oil, polyethylene glycol 4,000, polyethylene glycol 6,000, magnesium lauryl sulfate, etc.).

The excipient used in the preparation of emulsion is generally water, oil (e.g., fatty acid), emulsifier, and necessary preservative and flavoring agent.

The excipient used in the preparation of granule is similar to that for tablet, but the granulation process is different. The prepared granules are mixed with a glidant as needed, and then filled into capsules to obtain capsules.

As used herein, the term "subject," "organism," "animal," or "patient" includes human, wild animal, and livestock. Wild animal is an animal that is in natural state and has not been artificially domesticated. Livestock is an animal that is artificially raised to provide a source of food, such as, but not limited to, dog, cat, mouse, rat, hamster, pig, rabbit, cow, buffalo, bull, sheep, goat, geese, chicken and the like. The "patient" or "organism" to be treated preferably is a mammal, especially a human.

As used herein, the term "preventing" means that various means or measures are used for preventing the occurrence or development of a disease, including medical, physical or chemical means, to prevent and reduce occurrence or development of symptoms of various diseases before the disease is not recognized by clinical standards.

As used herein, the term "treating" refers to the inhibition, suppression, reduction, amelioration, mitigation, cessation, delay or reversal of the progression or aggravation of a disease for the prevention and suppression of the development or progression of the disease, and the described various indicators of disease, disorder, or pathology at the time of retention and/or administration include alleviating or reducing symptoms or complications, or curing or eliminating disease, disorder, or condition.

The term "medicament" as used herein refers to a single compound or a composition formed by a plurality of compounds which can be used for preventing or treating a disease; to a composition or a formulation having a single compound as a main active ingredient; and also to a composition or formulation that is composed of a plurality of compounds as active ingredients. The "medicament" should be understood to mean not only the products examined and approved for production by the administrative organization established by the laws of a country, but also various matter forms containing a single compound as the active ingredient formed in the process for obtaining approval and approval of production. The "formation" is understood to refer to obtainment by chemical synthesis, biotransformation or purchase.

The administration route of pharmaceutical composition provided by the present invention includes, but is not limited to, administration through oral, nasal, buccal, transdermal, pulmonal, vaginal, subcutaneous or intravenous route to the organism.

The main advantages of the present invention are as follows.

(1) The present invention firstly reveals the synergistic inhibitory effect of favipiravir and suramin, rupintrivir and itraconazole or favipiravir on enterovirus.

(2) The composition of the present invention takes effect with a low amount.

(3) The composition of the present invention can greatly reduce the clinical dosage, which can reduce the production cost and reduce the burden on the patient.

(4) The composition of the present invention can prevent the development of drug-resistant strains.

(5) The present invention firstly discloses a novel target for enterovirus.

The present invention will be further described in detail below with reference to specific examples. It should be understood that these examples are only for illustrating the present invention and are not intended to limit the scope of the present invention. The experimental methods in the following examples, which do not specify the detailed conditions, are usually in accordance with conventional conditions such as the conditions described in Guide to Molecular Cloning (Sambrook, J. et al., translated by Huang Peitang et al., Beijing: Science Press, 2002), or in accordance with the conditions recommended by the manufacturer. Unless otherwise indicated, percentages and parts are by weight. The experimental materials and reagents used in the following examples are available from commercially available sources unless otherwise specified.

Materials and Method
Cells, Viruses and Compounds RD (human rhabdomyomas) and Vero (African green monkey kidney) cells in DMEM medium containing 1% penicillin/streptomycin (P/S) and 10% fetal bovine serum (FBS) are cultured in a 37° C., 5% $CO_2$ incubator. EV71 FY573 strain (GenBank Accession No. HM064456) is used in the evaluation experiment for the antiviral activity of the compound, the viral titer reduction experiment, and combined medication experiment. EV71 G082 is used in the viral titer reduction experiment, mutant virus screening and evaluation experiment. Compounds itraconazole, rupintrivir, favipiravir and GW5074 are purchased from Sigma-Aldrich, Santa Cruz and Chembest, respectively, and dissolved in DMSO for experiments. Suramin is purchased from Bayer and dissolved in the medium.

Evaluation Experiment for Compounds

Itraconazole purchased from Sigma-Aldrich is dissolved in DMSO to a final concentration of 10 mM; suramin purchased from Bayer is dissolved in a medium containing 2% FBS to a final concentration of 50 mM; favipiravir purchased from Chembest is dissolved in DMSO to a final concentration of 400 mM; rupintrivir purchased from Santa Cruz is dissolved in DMSO to a final concentration of 2 mM; and GW5074 purchased from Sigma is dissolved in DMSO to a final concentration of 10 mM. To evaluate the inhibition of EV71-induced CPE activity by five compounds, the inventors perform dose dependent experiments. 50 μl of DMEM containing 10000 RD cells is added to each well of a 96-well white plate (Corning Costar), and after 24 hours of culture in a 37° C., 5% $CO_2$ incubator, a gradient dilution of the test compound is added to each well (for the compound dissolved in DMSO, the final concentration of DMSO is 0.25%), and 5 μl of 0.25% DMSO or medium is added to the control group. Then, 45 μl of dilution containing 150 PFU virus is added, and the final volume of each well is 100 After 96 hours of culture, the plate is taken out and equilibrated at room temperature for 30 minutes. Then, 50 μl of CellTiter-Glo (Promega) reagent is added to each well, and allowed to stand at room temperature for 10 to 30 minutes, and detected using a Veritas Microplate Luminometer (Turner BioSystem). In order to determine the effect of the compound on the cells, the inventors perform a cytotoxicity experiment in the same manner as the dose-dependent experiment except that no virus solution is added and an equal volume of DMEM containing 2% FBS and 1% P/S is added.

Combined Medication Experiment

In order to evaluate the inhibitory effect of the combination medication method on EV71 infection, the inventors carry out the experiment by checkerboard method[1-2]. 50 μl of DMEM containing 10000 RD cells is added to each well of a 96-well white plate (Corning Costar) and incubated in a 37° C., 5% $CO_2$ incubator for 24 h, and then 5 μl of two 2-fold diluted test compounds is added to the central 60 wells of a 96-well plate and 5 μl of 0.25% DMSO or medium is added to the control group. Then, 40 μl dilution containing 150 PFU virus is added, and the final volume of each well is 100 μl. After 96 hours of culture, the plate is taken out and equilibrated at room temperature for 30 minutes. Then, 50 μl of CellTiter-Glo (Promega) reagent is added to each well, and allowed to stand at room temperature for 10 to 30 minutes, and detected using a Veritas Microplate Luminometer (Turner BioSystem). In order to determine the effect of the simultaneous addition of two compounds on the cells, the inventors perform cytotoxicity experiment in the same manner as combined medication experiment except that no virus solution is added and an equal volume of DMEM containing 2% FBS and 1% P/S is added. The experimental results are analyzed using MacSynergy II software and a 3D schematic is obtained.

Determination of Viral Titer

The titers of EV71 G082 strain and the recombinant virus are measured, and 1 ml of DMEM containing $3\times10^5$ Vero cells is added to each well of a 12-well plate (Corning Costar), and cultured for 24 hours. The virus is diluted in 10-fold, that is, 27 μl of the virus solution is mixed with 243 μl DMEM containing 2% FBS and 1% P/S. The medium in the 12-well plate is aspirated, and 200 μl of virus solution is added to each well, then placed in a 37° C., 5% $CO_2$ incubator for 1 h of infection, and gently shaken every 15 minutes. Then, the virus solution is aspirated, and 1 ml DMEM containing 0.8% methylcellulose (Aquacide II, Calbiochem) and 2% FBS is added, cultured in a 37° C., 5% $CO_2$ incubator for 6 days, and placed in 3.7% formalin. After fixed for 1 h, it is stained with 1% crystal violet.

The titer of EV71 FY573 strain is determined by half of the tissue culture infectious dose ($TCID_{50}$). 20,000 RD cells are added to each well of a 96-well transparent plate. After 24 hours of culture, 100 μl of 10-fold diluted virus (from $10^{-1}$ to $10^{-8}$) is added to 10 wells for each dilution. After 1 h of infection, the virus is aspirated and DMEM containing 2% FBS is added. After 7 days of culture in a 37° C., 5% $CO_2$ incubator, the mixture is placed in 3.7% formalin for 1 h of fixation and then stained with 1% crystal violet. The viral titer is measured by Reed-Muench method and expressed as $TCID_{50}$/ml.

Viral Titer Reduction Experiment

RD cells are seeded in a 12-well plate with $3\times10^5$ cells/well, cultured overnight at 37° C. for 24 hours. Then EV71 virus solution with MOI=0.1 and 2-fold dilution of itraconazole, rupintrivir, favipiravir, suramin and GW5074 are added and cultured at 37° C. for 48 h. The supernatant is collected, frozen in a −80° C. refrigerator, and then determined for viral titer. To determine the resistance of the passaged virus to favipiravir, the inventors inoculate Vero cells in a 12-well plate, $3\times10^5$ cells/well and culture overnight at 37° C. After 24 hours, EV71 virus solution with MOI=0.1 is added and 300 μM and 600 μM favipiravir are separately added. After cultured at 37° C. for 48 hours, the supernatant is collected and frozen in a −80° C. refrigerator, and then the viral titer is measured.

Virus Screening Experiment

The present inventors conduct a passage experiment to screen a favipiravir resistant strain. $3\times10^5$ Vero cells are seeded in a 12-well plate, cultured overnight at 37° C. After 24 hours, EV71 G082 strain virus solution with MOI=0.1 and favipiravir are added. When a significant cytopathic effect is observed, the supernatant is collected. The pre-cultured Vero cells are infected with the collected virus and favipiravir is added. During the passage, the concentration of favipiravir is gradually increased, and one to three rounds of screening are carried out for each concentration with one control group for each round. After 16 continuous passages, the titer of the virus in the supernatant, the resistance to the compound, and sequencing are determined.

Mutant Virus Resistance Experiment

To determine the resistance of the selected mutant virus and recombinant virus to the compound, the inventors conduct experiments based on cytopathic effects and viral titer reduction experiments. In the experiment based on the cytopathic effect, 5000 Vero cells are added to each well of a 96-well white plate, and after incubated in a 37° C., 5% $CO_2$ incubator for 24 hours, a gradient dilution of the test compound is added to each well (for the compound dissolved in DMSO, the final concentration of DMSO is 0.25%), and 5 µl of 0.25% DMSO or medium is added to the control group. Then, 45 µl dilution containing 250 HU mutant virus or recombinant virus is added and the final volume of each well is 100 µl After 96 hours of culture, the plate is taken out and equilibrated at room temperature for 30 minutes. Then, 50 µl of CellTiter-Glo reagent is added to each well, allowed to stand at room temperature for 10 to 30 minutes, and detected using a Veritas Microplate Luminometer. EV71 G082 strain is served as a control.

In the viral titer reduction experiment, Vero cells are inoculated in a 12-well plate at $3\times10^3$ cells/well, and cultured overnight at 37° C. After 24 hours, EV71 virus solution with MOI=0.1 and 300 µM of favipiravir are added. The supernatant is collected after 48 hours of culture, and the viral titer is examined.

Construction of Mutant Virus

A plasmid containing the mutated DNA fragment is constructed using Fast Site-directed Mutagenesis kit (TransGen Biotech) according to the manufacturer's instructions and verified by sequencing. The correct cDNAs are linearized and transcribed into RNA according to in vitro transcription kit (MEGAscript T7 Kit, Ambion), which then transferred to Vero cells by electroporation. After the obvious CPE is observed, the supernatant is collected and the plaque assay is used to determine the viral titer.

RT-PCR

The viral RNA is extracted with reference to the instruction manual of QIAamp viral RNA minikit (Qiagen) and stored at −80 degrees, and the PCR reaction is carried out using a SuperScript III One-Step RT-PCR System with Platinum Tap DNA Polymerase (Invotroge).

Immunostaining Experiment

The present inventors perform immunostaining for qualitative detection of viruses in screening experiment of resistant strains. $3\times10^5$ Vero cells are pre-inoculated in 24-well plates, and cultured in a 37° C., 5% $CO_2$ incubator for 24 h, then virus stock and 10-fold diluted virus are added to each well and placed in a 37° C., 5% $CO_2$ incubator for 1 h of infection, and gently shaked every 15 minutes. The virus solution is then aspirated, and 1 ml of DMEM containing 0.8% methylcellulose (Aquacide II, Calbiochem) and 2% FBS is added, and cultured in an incubator at 37° C., 5% $CO_2$ for 6 days. The cells are fixed with 4% formaldehyde solution, and the fixed cells are washed twice with PBS containing 0.05% Tween-20 (PBS-T), incubated with primary antibody against enterovirus 71 (MAB979, Merck Milipore) for 1 h at room temperature, then washed for three times with PBS-T and incubated with horseradish peroxidase-conjugated secondary antibody (goat anti-mouse, Bethyl, Montgomery, Tex.) for 1 h at room temperature. After the plate is washed for 3 times with PBS, TrueBlue peroxidase substrate (KPL®, 50-78-02) is added for development. When clear blue spots are formed in the control group, the reaction is stopped with distilled water. The plate is dried, and the results are recorded. Cells that produce blue are positive, and cells that do not produce blue do not contain viruses.

Data Analysis

The raw data are input into an Excel sheet to calculate the signal-to-background ratio (S/B), the signal-to-noise ratio (S/N), Z factor, and the inhibition rate of the test compound against the virus. The calculation formulas are as follows: $S/B=\mu_c/\mu_v$, wherein $\mu_c$ represents the average value of the signal of the cell control group, and $\mu_v$ represents the average value of the signal of the virus control group; $S/N=(\mu_c-\mu_v)/(\sigma_c-\sigma_v)$, $\sigma_c$ represents the standard deviation of the signal of the cell control group, and $\sigma_v$ represents the standard deviation of the signal of the virus control group; $Z=1-((3\sigma_c+3\sigma_v)/|\mu_c-\mu_v|)$, when Z factor is between 0.5 and 1, it indicates that the experimental method can effectively distinguish the differences between control groups. The antiviral activity of the compound CPE inhibition rate= $(\mu_{cpd}-\mu_v)/(\mu_c-\mu_v)\times100\%$, wherein $\mu_{cpd}$ represents the average signal intensity of the test compound; and the effect of the compound on the cell, cell survival rate=$\mu_{cpd}/\mu_c\times100\%$. The half maximum effect concentration ($EC_{50}$) is a concentration that causes a 50% maximum effect. The half-cytotoxic concentration ($CC_{50}$) refers to a concentration of the medicament that causes 50% cytotoxicity, which is expressed in this experiment as a 50% reduction in the fluorescence intensity of the experimental group compared with the control group. In the analysis of the interaction effects of the two compounds using Macsnergy II, at 95% confidence, a volume greater than zero represents that the interaction of the two compounds is a synergistic effect, and a negative value represents an antagonistic effect. Value between −25 and +25 indicates that the effect between the two compounds is not significant, value between 25 and 50 represents significant but weak synergy, value between 50 and 100 means moderate synergy, and value greater than 100 indicates strong synergy.

Example 1 Single Component Activity Assay

Itraconazole, rupintrivir, favipiravir, suramin, and GW5074 are effective in inhibiting EV71 infection of cells in a dose-dependent manner.

Figure 1A:
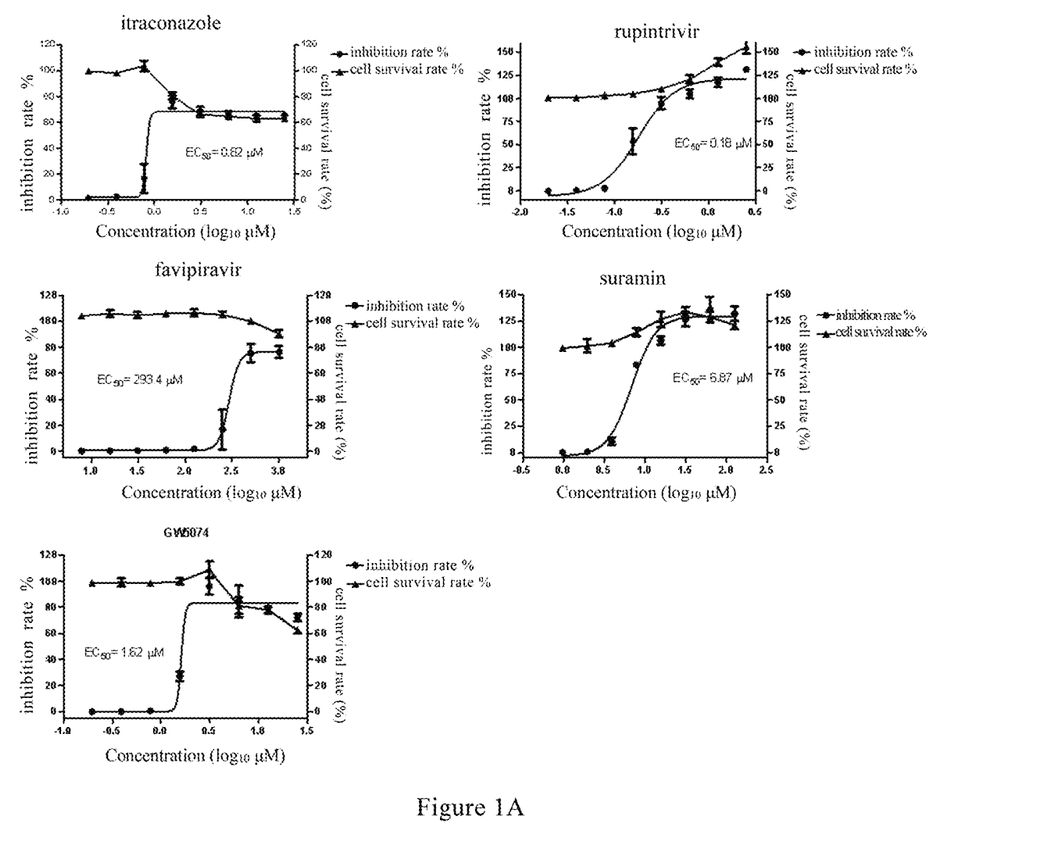
FIG. 1A shows the inhibitory effect of each compound on EV71 and toxic effects thereof on cells.
Figure 1B:
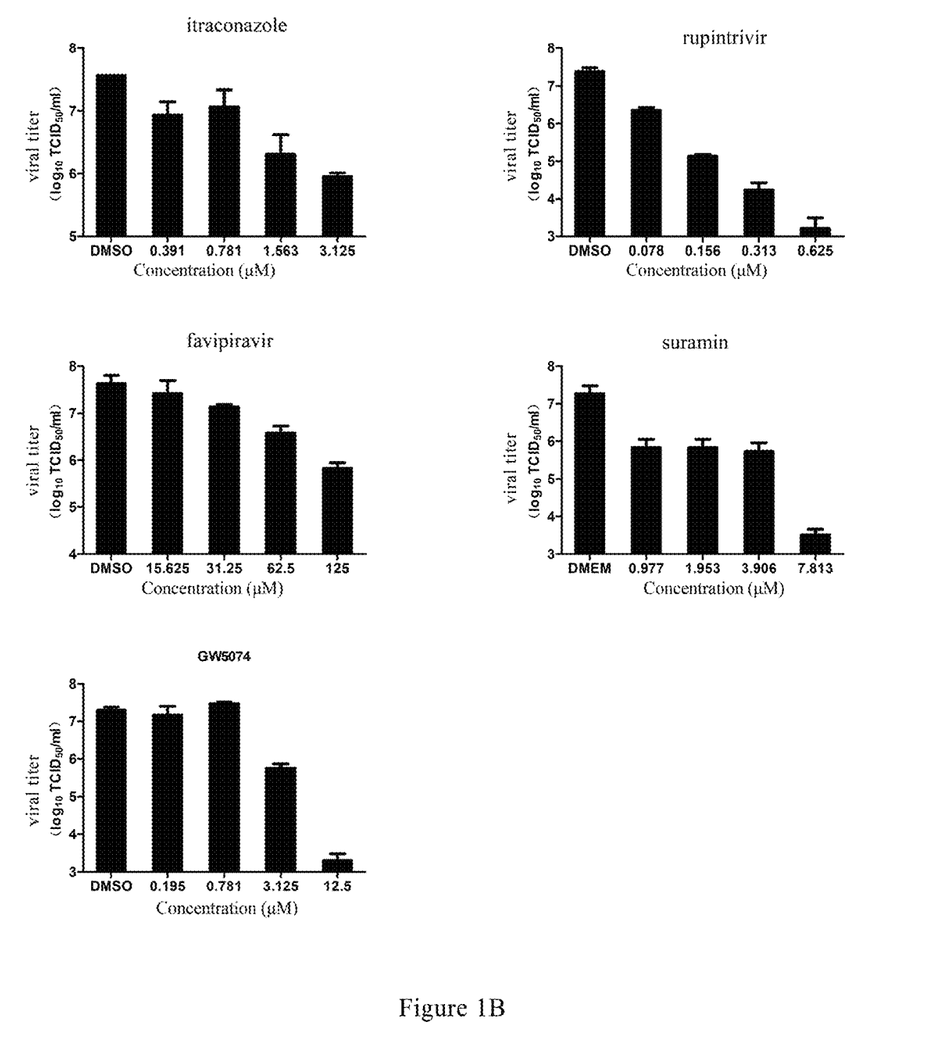
FIG. 1B shows the effect of different concentrations of each compound on viral titer.

FIG. 1 shows that itraconazole, rupintrivir, favipiravir, suramin, and GW5074 inhibit EV71 infection. (A) 2-fold dilution of itraconazole, rupintrivir, favipiravir, suramin, and GW5074 were separately added to RD cells, and virus or medium was added and cultured for 96 hours. The cell viability was measured by CellTiter-Glo kit. The inhibitory effects of four compounds on EV71 and the toxic effects on cells were examined. (B) Virus and 2-fold dilution of itraconazole, rupintrivir, favipiravir, suramin, and GW5074 were separately added into RD cells. After 48 hours of culture, the supernatant was collected and the viral titer was determined by $TCID_{50}$ method. The results were processed using Graphpad Prism5. The data in the figure were obtained from two independent parallel experiments, and the error bars represent the standard deviation of the two parallel experiments.

Example 2 Favipiravir Acts on 3D Protein of Enterovirus 71

The present inventors obtained two strains of resistant viruses by screening viruses resistant to favipiravir. The viral titer reduction experiment showed that both strains were resistant to favipiravir, and the inventors found that the same mutation occurred on the 3D protein by sequence analysis. The drug-resistant virus phenotype experiment demonstrated that EV71 having amino acid residue mutation at position 121 in the 3D protein was resistant to favipiravir. Using the reverse genetics system, the inventors constructed a virus carrying such mutation and had its resistance to favipiravir verified. The results showed that the mutation of serine to aspartic acid at position 121 of 3D protein of enterovirus 71 conferred drug-resistance to EV71, and the present inventors inferred that favipiravir acted on 3D protein of EV71. Furthermore, the present inventors tested the inhibitory effect of itraconazole, rupintrivir, suramin, and GW5074 on the mutant virus, and compared with the wild type virus (G082), no cross-resistance was found. The results were shown in FIG. 2.

Figure 2:
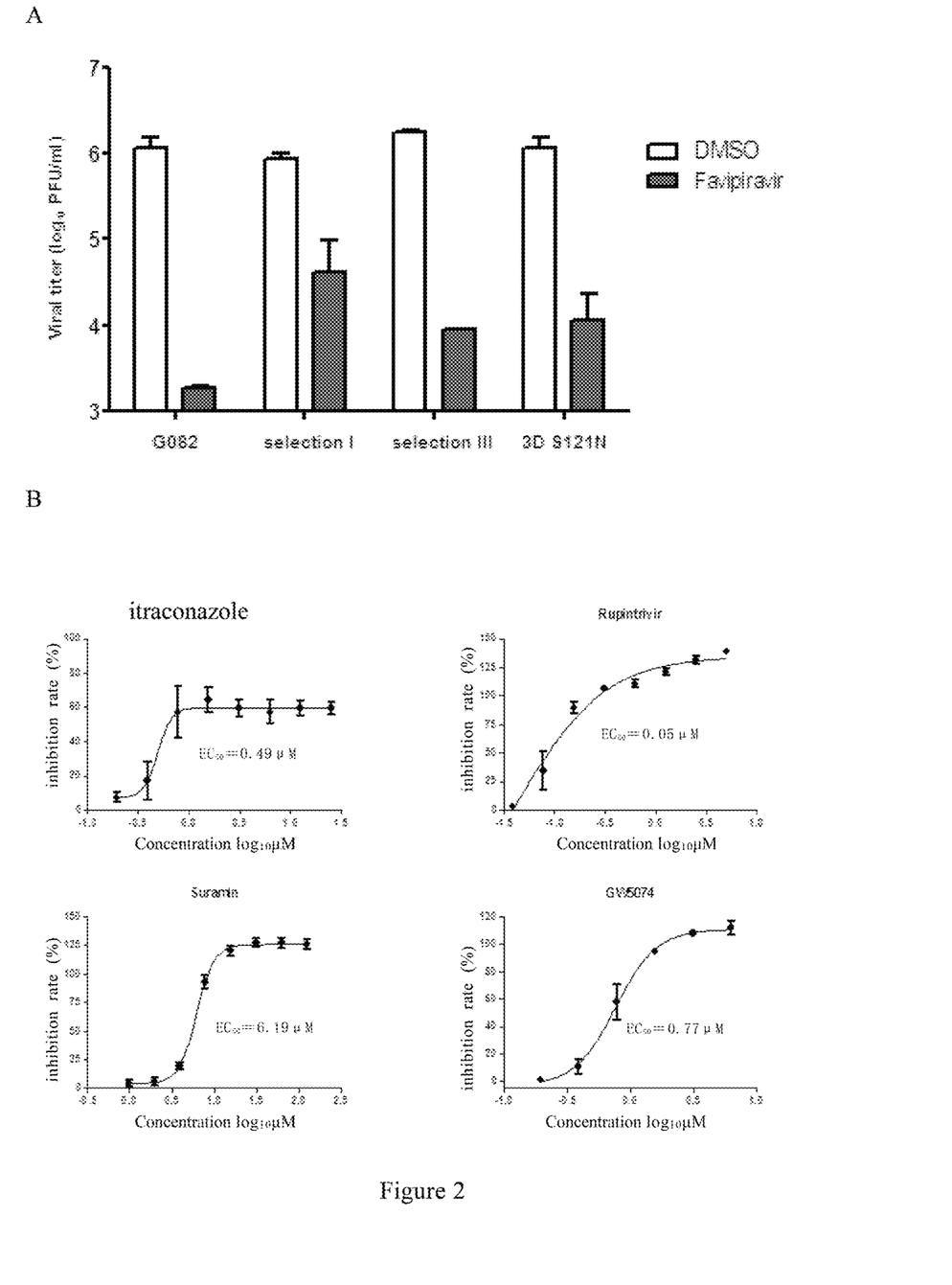
FIG. 2 shows that favipiravir inhibits virus replication by acting on 3D protein of enterovirus 71.

FIG. 2 shows that favipiravir inhibits viral replication by acting on 3D protein of enterovirus 71. (A) Enterovirus 71 was incubated with favipiravir and the concentration of favipiravir was continually increased. The supernatant from the 16$^{th}$ passage culture was collected and sequenced. EV71 containing 3D protein mutation was constructed by reverse genetics system. The viral titer was determined by plaque formation assay, the virus resistance to favipiravir was detected by viral titer reduction experiment. The experimental method was the same as the compound verification experiment. (B) The effects of itraconazole, rupintrivir, suramin and GW5074 on a virus containing 3D protein mutation were determined using an experiment based on cytopathic effect. The results were processed using Graphpad Prism5. The data in the figure were obtained from two independent parallel experiments, and the error bars represent the standard deviation of the two parallel experiments.

Example 3 Combined Activity Assay

The combination of itraconazole, rupintrivir, favipiravir, suramin, and GW5074 produces synergistic, additive or antagonistic effects in the treatment of EV71 infection. The results are shown in FIG. 3.

Figure 3:
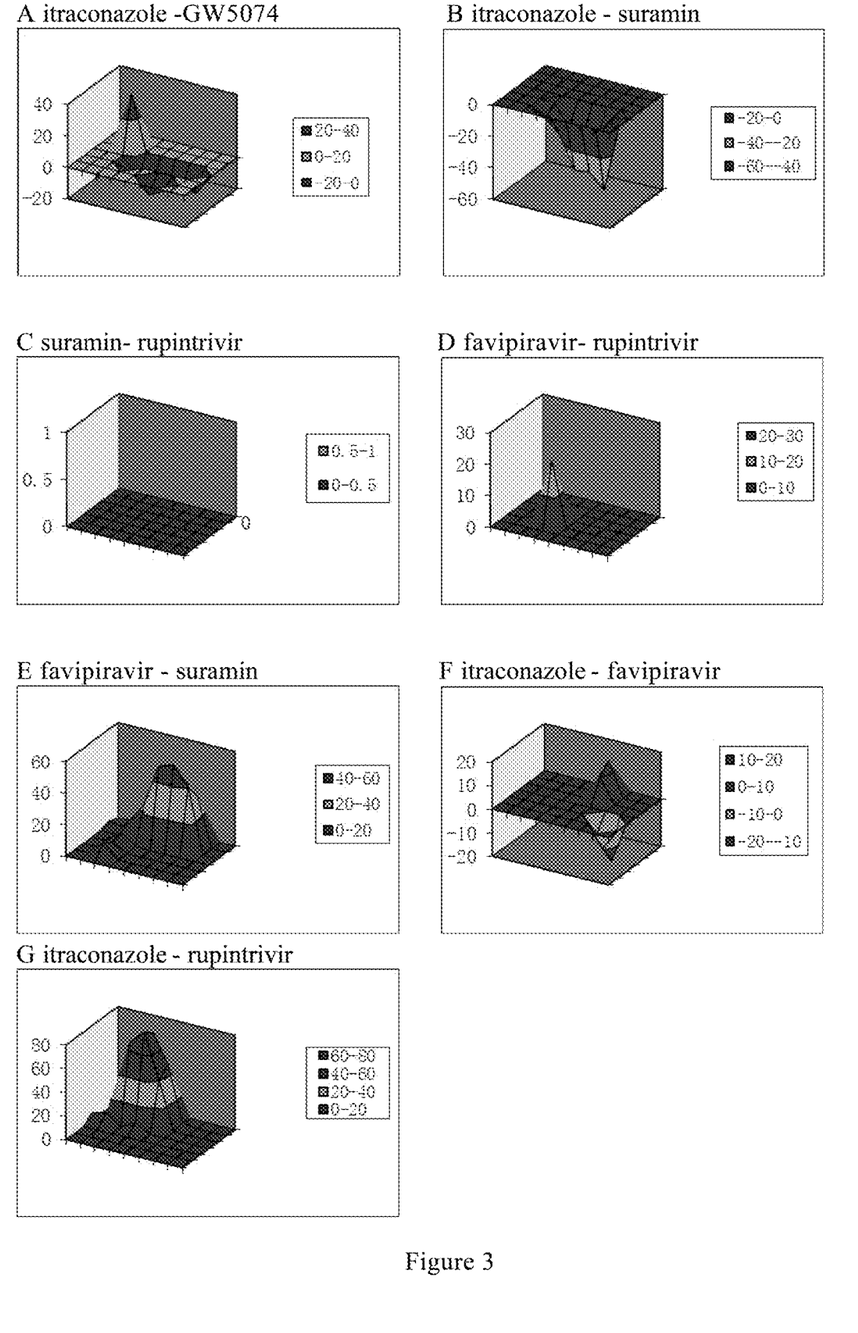
FIG. 3 shows the interaction effect of different medicament combinations on the treatment of EV71 infection.

FIG. 3 shows that the interaction effect of different medicament combinations in the treatment of EV71 infection. 3D plot was made using MacSynergy II software and the data in the plot were obtained from at least three independent parallel experiments. (A) combination of itraconazole and GW5074, (B) combination of itraconazole and suramin, (C) combination of suramin and rupintrivir, (D) combination of favipiravir and rupintrivir, (E) combination of favipiravir and suramin, (F) combination of favipiravir and itraconazole, and (6) combination of itraconazole and rupintrivir. The horizontal plane represents the additive effect of the two medicaments, the points above the horizontal plane represent the synergistic effect of the two medicaments, and the points below the horizontal plane represent the antagonistic effect.

TABLE 1

| Medicament combination | | MacSynergy II analysis Synergy/antagonism ($\mu M^2$ %) | Effect |
|---|---|---|---|
| itraconazole | rupintrivir | 434.44/−4.4 | strong synergy |
| itraconazole | favipiravir | 34.51/−88.11 | strong antagonism |
| itraconazole | suramin | 0.14/−246.23 | strong antagonism |
| rupintrivir | favipiravir | 64.9/0 | weak synergy |
| rupintrivir | suramin | 4.96/0 | additive effect |
| favipiravir | suramin | 337.59/0 | strong synergy |
| itraconazole | GW5074 | 53.91/−167.68 | strong antagonism |

Table 1 shows the synergistic, additive or antagonistic results calculated according to MacSynergy II software.

Example 4 Itraconazole and Rupintrivir Synergistically Inhibit Viral Titer

Itraconazole and rupintrivir are not only able to inhibit the cytopathic effects produced during viral infection, but also synergistically inhibit viral production. The results are shown in FIG. 4.

Figure 4:
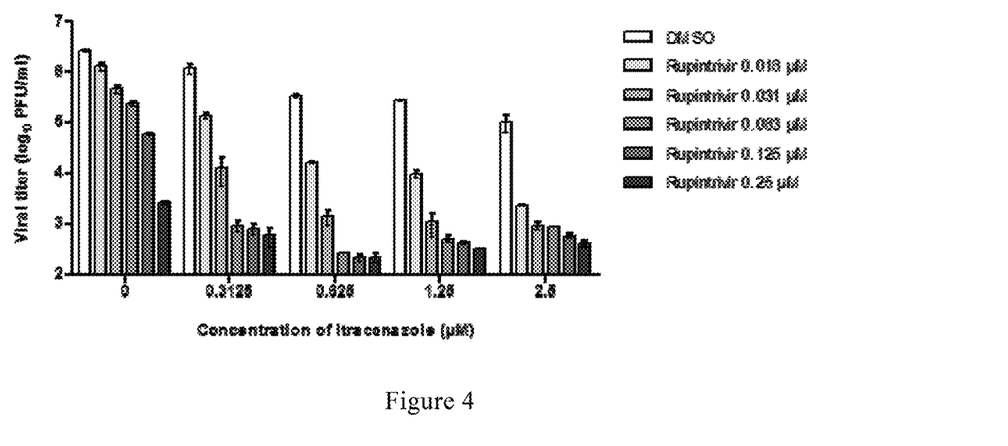
FIG. 4. shows that the combination of itraconazole and rupintrivir can synergistically inhibit EV71 titer.

FIG. 4 shows that the combination of itraconazole and rupintrivir can synergistically inhibit EV71 titer. EV71 with a multiplicity of infection (MOI) of 0.1 and different concentrations of itraconazole, rupintrivir or DMSO were added to Vero cells, and the supernatant was collected after 48 hours of culture, and the viral titer was detected by plaque formation assay. The results were processed using Graphpad Prism5. The data in the figure were obtained from two independent parallel experiments, and the error bars represent the standard deviation of the two parallel experiments.

Example 5 Analysis of the Interaction of Rupintrivir and Itraconazole in Combined Medication by Chou-Talalay Method Using the Compusyn software, the interaction between itraconazole and rupintrivir was analyzed according to the Chou-Talalay method, and it was found that the two compounds produced synergistic effect. And the synergistic effect was most obvious when the molar concentration ratio was itraconazole/rupintrivir=10/1. The results are shown in Table 2.

TABLE 2

| molar concentration ratio of itraconazole/ rupintrivir | % Inhibition rate ($ED_n$) | CI | DRI itraconazole | rupintrivir |
|---|---|---|---|---|
| 1:0.1 | 50 | 0.01(very strong synergy) | 285.689 | 138.384 |
|  | 75 | 0.02(very strong synergy) | 212.177 | 89.313 |
|  | 90 | 0.02(very strong synergy) | 157.582 | 57.642 |
|  | 95 | 0.03(very strong synergy) | 128.717 | 42.795 |
| 1:0.05 | 50 | 0.21(strong synergy) | 9.514 | 9.217 |
|  | 75 | 0.21(strong synergy) | 10.341 | 8.706 |
|  | 90 | 0.21(strong synergy) | 11.241 | 8.224 |
|  | 95 | 0.21(strong synergy) | 11.897 | 7.911 |

Table 2. EV71 was added to Vero cells and co-cultured with different concentrations of itraconazole and rupintrivir or DMSO. After 48 hours, the supernatant was collected and the viral titer was determined by plaque formation assay. The inhibitory effect of different concentration combinations on EV71 infection was obtained by comparison with the control group. The interaction between the two medicaments at the n % inhibition effect was analyzed using Compusyn software, and CI (combination index) and DRI (dose reduction index) were used as evaluation parameters. CI<0.1 indicates a very strong synergistic effect, and 0.1<CI<0.3 indicates a strong synergistic effect. DRI indicates the degree (fold) of the decrease in the concentration required for the two compounds in combined medication to achieve the same inhibitory effect as compared with one compound used in antiviral therapy. The data in the figure were obtained from two independent parallel experiments.

Example 6 Combination of Itraconazole and Rupintrivir can Prevent the Emergence of Drug-Resistant Viruses and Eliminate all Viruses EV71, itraconazole, and 0.5 μM or 1 μM of rupintrivir were simultaneously added to Vero cells, the virus was subcultured, and the supernatant was collected. After 20 passages, the inventors examined the viruses in the supernatants of the 10$^{th}$, 16$^{th}$ and 20$^{th}$ passage by immunostaining experiments, and no virus was detected. The viral titer reduction experiment proved that itraconazole could not remove all the viruses in the cell culture. The experimental results showed that the combination of itraconazole and rupintrivir prevented the emergence of drug-resistant viruses and completely inhibit the replication of EV71 in vitro.

All references mentioned in this application are incorporated by reference in this application, as if each were incorporated by reference individually. In addition, it should be understood that after reading the above teachings of the present invention, those skilled in the art can make various changes or modifications to the present invention, and these equivalent forms also fall within the scope defined by the appended claims of the present application.

REFERENCES

Furuta Y, Gowen B B, Takahashi K, Shiraki K, Smee D F, Barnard D L. Favipiravir (T-705), a novel viral RNA polymerase inhibitor. Antiviral Res 2013; 100:446-454.

Prichard M N, Prichard L E, Baguley W A, Nassiri M R, Shipman C, Jr. Three-dimensional analysis of the synergistic cytotoxicity of ganciclovir and zidovudine. Antimicrob Agents Chemother 1991; 35:1060-1065.

The invention claimed is:

1. A composition for inhibiting enterovirus, wherein the composition includes a first active ingredient and a second active ingredient,
    wherein the first active ingredient is an inhibitor of 3C protein of enterovirus (eg, EV71);
    the second active ingredient is an inhibitor of 3A protein of enterovirus (eg, EV71);
    wherein the inhibitor of 3C protein of enterovirus (eg, EV71) is rupintrivir, an analog thereof, or a pharmaceutically acceptable salt thereof; and
    the inhibitor of 3A protein of enterovirus (eg, EV71) is itraconazole, an analog thereof, or a pharmaceutically acceptable salt thereof, and
    wherein a molar ratio of the first active ingredient to the second active ingredient is about 1-20:10-100.

2. The composition of claim 1, wherein the first active ingredient specifically binds to an amino acid residue at position 121 of 3D protein of enterovirus, wherein the amino acid residue is numbered based on SEQ ID NO: 1.

3. The composition of claim 1, wherein the analog of rupintrivir includes a substance which acts on the same target of enterovirus as rupintrivir (eg, AG7404); and/or
    the analog of itraconazole includes a substance which acts on the same target of enterovirus as itraconazole.

4. The composition of claim 1, wherein the molar ratio of the first active ingredient to the second active ingredient is about 1-10:10-100.

5. The composition of claim 1, wherein the molar ratio of the first active ingredient to the second active ingredient is 1-5:10-100.

6. The composition of claim 1, wherein the dosage form of the pharmaceutical composition is a tablet, granule, capsule, pill, injection, or oral solution.

7. The composition of claim 1, wherein the composition is a unit dosage form, and the content of the first active ingredient and the second active ingredient in each unit dosage form is 0.1-1 of a daily dose, wherein the daily dose is 20-100 mg.

8. The composition of claim 2, wherein the amino acid residue is a serine residue.

* * * * *

SEQUENCE LISTING

```
<160> NUMBER OF SEQ ID NOS: 1

<210> SEQ ID NO 1
<211> LENGTH: 462
<212> TYPE: PRT
<213> ORGANISM: Enterovirus

<400> SEQUENCE: 1

Gly Glu Ile Gln Trp Val Lys Pro Asn Lys Glu Thr Gly Arg Leu Asn
1               5                   10                  15

Ile Asn Gly Pro Thr Arg Thr Lys Leu Glu Pro Ser Val Phe His Asp
                20                  25                  30

Ile Phe Glu Gly Asn Lys Glu Pro Ala Val Leu His Ser Lys Asp Pro
            35                  40                  45

Arg Leu Glu Val Asp Phe Glu Gln Ala Leu Phe Ser Lys Tyr Val Gly
    50                  55                  60

Asn Thr Leu Tyr Glu Pro Asp Glu Tyr Ile Lys Glu Ala Ala Leu His
65                  70                  75                  80

Tyr Ala Asn Gln Leu Lys Gln Leu Glu Ile Asn Thr Ser Gln Met Ser
                85                  90                  95

Met Glu Glu Ala Cys Tyr Gly Thr Glu Asn Leu Glu Ala Ile Asp Leu
            100                 105                 110

His Thr Ser Ala Gly Tyr Pro Tyr Ser Ala Leu Gly Ile Lys Lys Arg
        115                 120                 125

Asp Ile Leu Asp Pro Thr Thr Arg Asp Val Ser Lys Met Lys Phe Tyr
    130                 135                 140

Met Asp Lys Tyr Gly Leu Asp Leu Pro Tyr Ser Thr Tyr Val Lys Asp
145                 150                 155                 160

Glu Leu Arg Ser Ile Asp Lys Ile Lys Lys Gly Lys Ser Arg Leu Ile
                165                 170                 175

Glu Ala Ser Ser Leu Asn Asp Ser Val Tyr Leu Arg Met Thr Phe Gly
            180                 185                 190

His Leu Tyr Glu Ala Phe His Ala Asn Pro Gly Thr Ile Thr Gly Ser
        195                 200                 205

Ala Val Gly Cys Asn Pro Asp Thr Phe Trp Ser Lys Leu Pro Ile Leu
    210                 215                 220

Leu Pro Gly Ser Leu Phe Ala Phe Asp Tyr Ser Gly Tyr Asp Ala Ser
225                 230                 235                 240

Leu Ser Pro Val Trp Phe Arg Ala Leu Glu Leu Val Leu Arg Glu Ile
                245                 250                 255

Gly Tyr Ser Glu Arg Ala Val Ser Leu Ile Glu Gly Ile Asn His Thr
            260                 265                 270

His His Val Tyr Arg Asn Lys Thr Tyr Cys Val Leu Gly Gly Met Pro
        275                 280                 285

Ser Gly Cys Ser Gly Thr Ser Ile Phe Asn Ser Met Ile Asn Asn Ile
    290                 295                 300
```

```
Ile Ile Arg Ala Leu Leu Ile Lys Thr Phe Lys Gly Ile Asp Leu Asp
305                 310                 315                 320

Glu Leu Asn Met Val Ala Tyr Gly Asp Asp Val Leu Ala Ser Tyr Pro
            325                 330                 335

Phe Pro Ile Asp Cys Leu Glu Leu Ala Lys Thr Gly Lys Glu Tyr Gly
            340                 345                 350

Leu Thr Met Thr Pro Ala Asp Lys Ser Pro Cys Phe Asn Glu Val Asn
        355                 360                 365

Trp Gly Asn Ala Thr Phe Leu Lys Arg Gly Phe Leu Pro Asp Glu Gln
    370                 375                 380

Phe Pro Phe Leu Ile His Pro Thr Met Pro Met Arg Glu Ile His Glu
385                 390                 395                 400

Ser Ile Arg Trp Thr Lys Asp Ala Arg Asn Thr Gln Asp His Val Arg
            405                 410                 415

Ser Leu Cys Leu Leu Ala Trp His Asn Gly Lys Gln Glu Tyr Glu Lys
            420                 425                 430

Phe Val Ser Thr Ile Arg Ser Val Pro Val Gly Arg Ala Leu Ala Ile
            435                 440                 445

Pro Asn Tyr Glu Asn Leu Arg Arg Asn Trp Leu Glu Leu Phe
    450                 455                 460
```